(12) United States Patent
Duffy

(10) Patent No.: US 6,191,072 B1
(45) Date of Patent: Feb. 20, 2001

(54) HERBICIDAL CUTTING LINE

(76) Inventor: Niall Duffy, 234 Pleasant St., Arlington, MA (US) 02476-8134

( * ) Notice: Under 35 U.S.C. 154(b), the term of this patent shall be extended for 0 days.

(21) Appl. No.: 09/217,881

(22) Filed: Dec. 21, 1998

(51) Int. Cl.[7] ..................................................... A01N 25/34
(52) U.S. Cl. ........................... 504/360; 428/378; 428/396
(58) Field of Search ..................................... 428/378, 396; 504/360

(56) References Cited

U.S. PATENT DOCUMENTS

| | | | |
|---|---|---|---|
| 3,864,114 | * | 2/1975 | Green .......................................... 71/3 |
| 3,994,437 | * | 11/1976 | Kitterman ................................. 239/1 |
| 4,405,360 | * | 9/1983 | Cardarelli ................................. 71/117 |
| 5,665,822 | * | 9/1997 | Bitler et al. ......................... 525/92 C |

* cited by examiner

*Primary Examiner*—S. Mark Clardy
(74) *Attorney, Agent, or Firm*—Hamilton, Brook, Smith & Reynolds P.C.; Rodney D. Johnson

(57) ABSTRACT

A cutting line for a rotating-line trimmer that simultaneously applies herbicide as vegetation is cut. The herbicidal cutting line comprises a flexible cutting-line core (13) herbicidal coating (15) that covers all or part of the line core and a thin protective shield (17) covering all or part of the herbicidal coating. As vegetation is cut, protective shield (17) ruptures exposing herbicidal coating (15) to vegetation. The cutting line is used with existing line trimmers in applications in which vegetation regrowth is objectionable.

28 Claims, 3 Drawing Sheets

HERBICIDAL CUTTING LINE

BACKGROUND—FIELD OF THE INVENTION

This invention relates to rotating-flexible-line trimmers specifically to a cutting line that simultaneously applies herbicide as vegetation is cut.

BACKGROUND—DESCRIPTION OF PRIOR ART

Rotating line trimmers have gained widespread popularity for trimming vegetation in hard-to-reach places such as next to buildings, fences, trees, and shrubs. Such trimmers typically include a rotating hub from which a cutting line is radially dispensed. Preferably, the line is flexible to increase the safety of the trimmer. As the hub is rotated, the resulting centrifugal force causes the line to extend substantially straight out from the hub. The line, being rotated at high speeds serves as a cutting surface similar to a blade. Applications can be divided into two basic categories:

(1) removal of unwanted vegetation and
(2) trimming of desired vegetation.

The present invention addresses the first category, removal of unwanted vegetation. Examples include weeds in walkways, driveways, between pavers, and on other paved surfaces. In these situations complete and permanent removal is desired. For this reason, unwanted vegetation is trimmed as close to the root as possible. Nevertheless, weed roots remain intact and regrowth may occur.

Currently, the options for clearing unwanted vegetation are limited. Vegetation may be sprayed with herbicide; however, the kill process may take considerable time, from days to weeks. After vegetation has expired, dead vegetation must be removed. A further disadvantage of herbicide spraying is that overspray and dripping may cause unnecessary environmental impact.

The line trimmer provides a second option, severing unwanted vegetation from the root. The advantage of this approach is that cut vegetation can be removed immediately by sweeping with a push brush or a broom. The disadvantage is that vegetation roots remain intact and may regrow. Consequently, the trimming job must be repeated frequently due to vegetation regrowth.

As such, there is need for a device that simultaneously trims vegetation and applies herbicide.

OBJECTS AND ADVANTAGES

Accordingly, several objects and advantages of my invention are:

(a) to provide a cutting line that simultaneously applies herbicide as vegetation is trimmed;
(b) to provide an alternative to herbicide spraying that reduces herbicide usage thereby limiting environmental impact;
(c) to provide an alternative to herbicide spraying that severs vegetation from the root thereby permitting immediate removal;
(d) to provide a cutting line that keeps driveways, walkways, and patios weed-free for extended periods of time; and
(e) to provide a new herbicide product that appeals to a wide range of consumers including homeowners with casual gardening interests.

DRAWING FIGURES

Figure 1A:
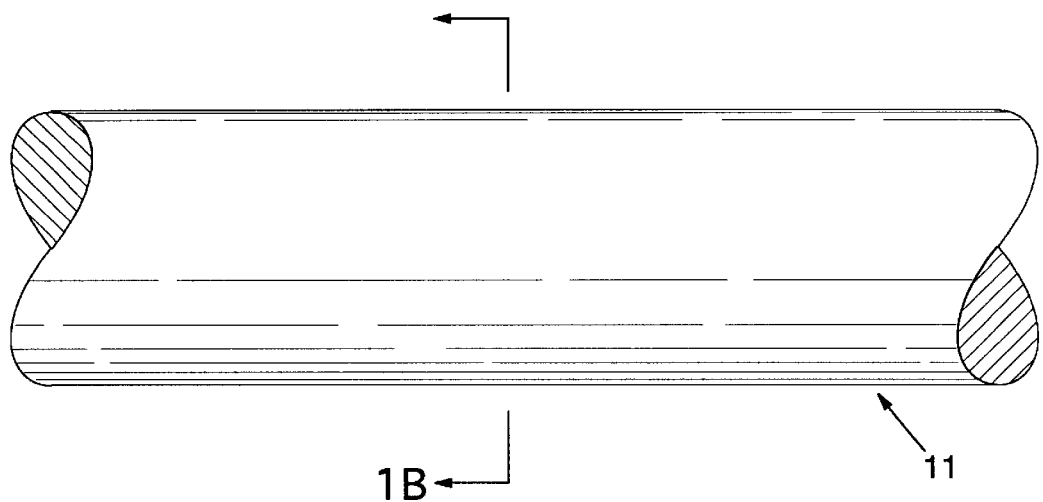
FIG. 1A shows a front side view of a preferred embodiment of a herbicidal cutting line.

REFERENCE NUMERALS IN DRAWINGS 11 herbicidal cutting line
13 flexible-cutting-line core
15 herbicidal coating
17 protective shield
19 rotating hub (not part of present invention)
23 fibrous material
25 herbicidal composition
27 protective shield
35 extruded monofilament line of a herbicidal composition
37 protective shield

SUMMARY

In accordance with the present invention a herbicidal cutting line comprises a flexible-line core coated with a herbicidal composition whereby herbicide is applied as vegetation is trimmed.

Figure 1B:
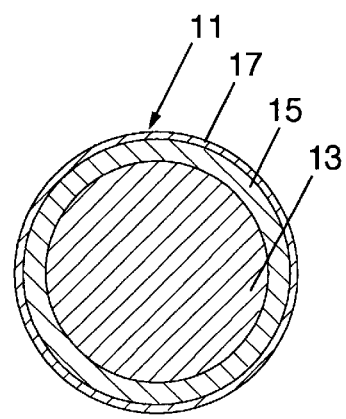
FIG. 1B shows a cross-sectional view of the embodiment of FIG. 1A.
Figure 1C:
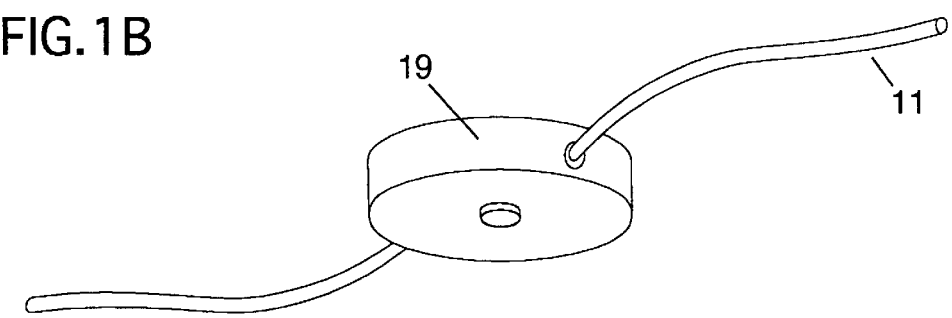
FIG. 1C shows a perspective view of the embodiment of FIG. 1A as it would appear in use attached to a rotating hub.

Description—FIGS. 1 to 3

A cutting line with a herbicidal coating is illustrated in FIGS. 1A and 1B. FIG. 1A shows a side view of a herbicidal cutting line. FIG. 1B shows a sectional view of cutting line 11. In this embodiment, cutting line 11 comprises a flexible-cutting-line core 13, a herbicidal coating 15 covering all or part of cutting-line core 13, and a protective shield 17 covering herbicidal coating 15. In use, the cutting line is dispensed from a rotating hub 19.

Cutting-line core 13 consists of a flexible line, not unlike conventional cutting line. In the preferred embodiment core 13 is a monofilament of extruded polymeric material, such as nylon, polyethylene, or polypropylene. The surface of core 13 may be scored or otherwise textured to promote adhesion of herbicidal coating 15.

A number of possibilities exist for herbicidal coating 15 including:

(a) a viscous liquid substance containing herbicide;
(b) a composition with a waxy consistency containing herbicide whereby herbicide residue remains on vegetation after contact; and
(c) a water soluble herbicide composition in which moisture from cut vegetation dissolves herbicide.

Herbicidal material 15 is covered with a protective shield 17 to prevent transmission of herbicide to line trimmer components, and hands during line replacement. Protective shield 17 comprises a soft, flexible, material that is impermeable to herbicidal coating 15. Protective shield 17 is sufficiently thin and soft such that it ruptures as cutting line 11 cuts vegetation, thereby exposing herbicidal coating 15. Protective shield 17 comprises a thin layer of polymeric material such as wax, polyethylene or polypropylene.

Figure 2A:
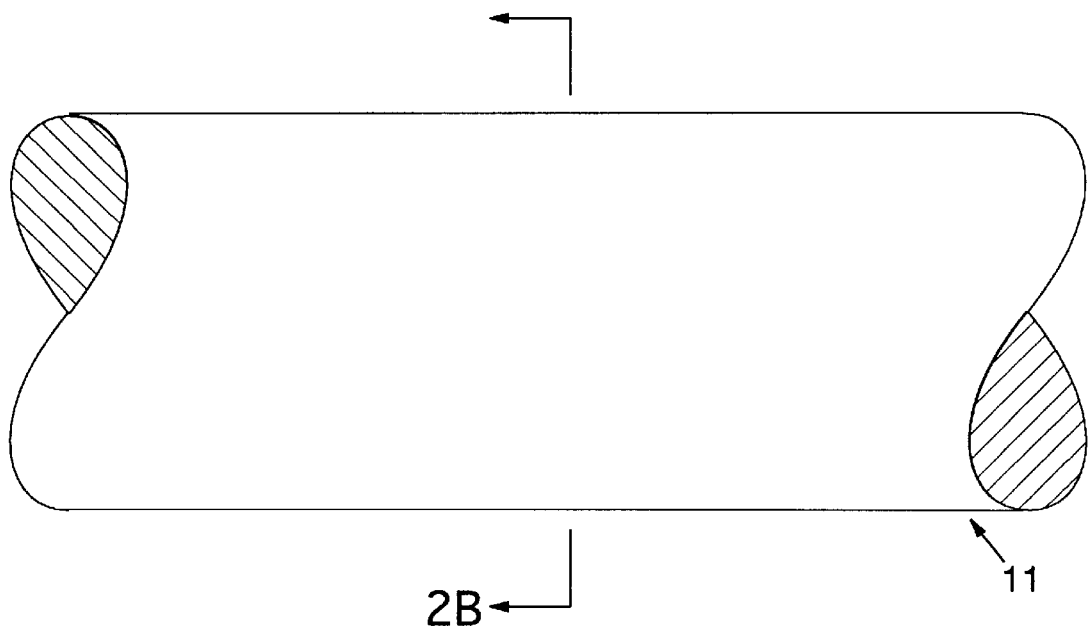
FIG. 2A shows a front side view of another embodiment of a herbicidal cutting line.
Figure 2B:
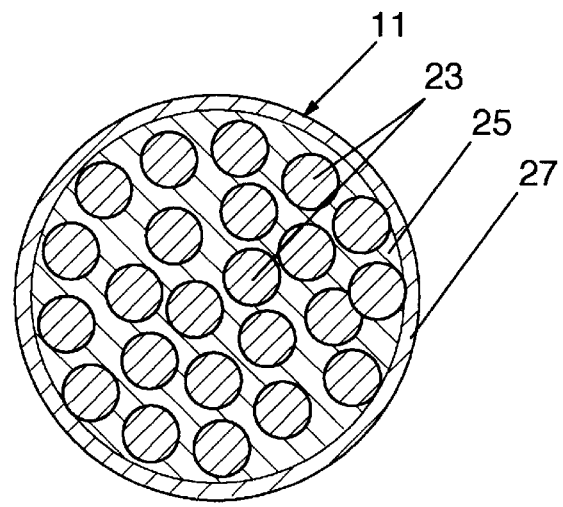
FIG. 2B shows a cross-sectional view of the embodiment of FIG. 2A.

FIGS. 2A and 2B show a second embodiment of herbicidal cutting line in which cutting line 11 comprises a fibrous material 23 impregnated with a herbicide composition 25. Fibrous material 23 consists of cotton, rayon, nylon, dacron, kevlar, or polypropylene. Herbicide composition 25 has a consistency that is soft enough to leave a residue on cut vegetation and to maintain line flexibility.

Herbicidal material 25 is covered with a protective shield 27 to prevent transmission of herbicide to line trimmer components, and hands during line replacement. Protective shield 27 comprises a soft, flexible, material that is impermeable to herbicidal composition 25. Protective shield 27 is sufficiently thin and soft such that it ruptures as cutting line 11 cuts vegetation, thereby exposing herbicidal composition 25. Protective shield 27 comprises a thin layer of polymeric material such as wax, polyethylene or polypropylene.

Figure 3A:
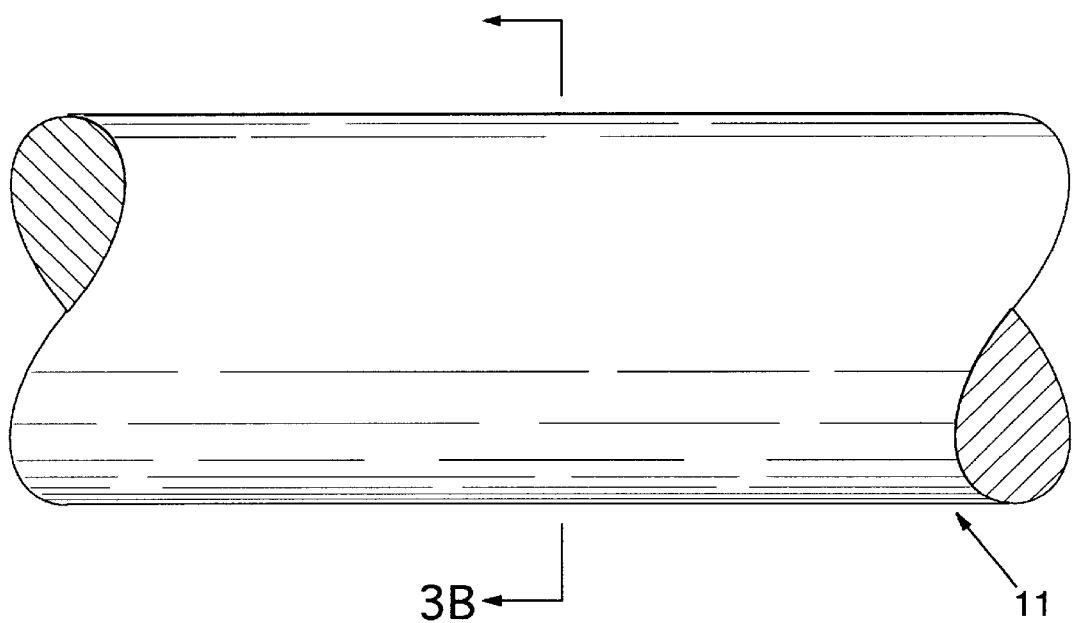
FIG. 3A shows a front side view of another embodiment of a herbicidal cutting line.
Figure 3B:
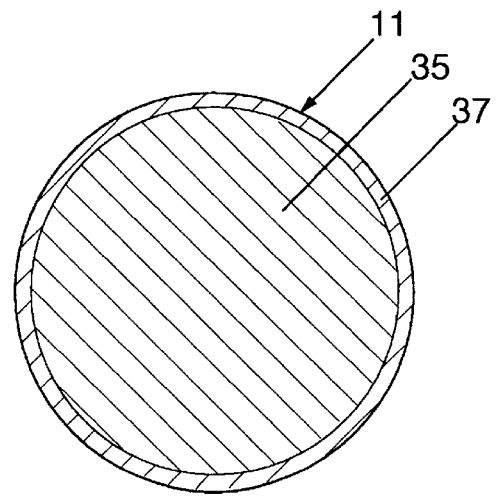
FIG. 3B shows a cross-sectional view of the embodiment of FIG. 3A.

FIGS. 3A and 3B show a third embodiment of herbicidal cutting line in which the cutting line comprises an extruded monofilament line of a herbicidal composition 35.

Monofilament line 35 is covered with a protective shield 37 to prevent transmission of herbicide to line trimmer components, and hands during line replacement and unreeling. Protective shield 37 comprises a soft, flexible, material that is impermeable to herbicidal composition 35. Protective shield 37 is sufficiently thin and soft such that it ruptures as cutting line 11 cuts vegetation thereby exposing herbicidal composition 35. Protective shield 37 comprises a thin layer of polymeric material such as wax, polyethylene or polypropylene.

Not all types of herbicide are effective for use in herbicidal cutting lines. For example, some contact herbicides do not have the mobility required to move from the application site (the cut) to the roots. Herbicides that work by disrupting cell membranes such as Bipyridyliums are poor choices for herbicidal cutting line.

Systemic herbicides that move within the plant via the phloem are generally effective for use in herbicidal cutting lines. Some examples include growth regulators (Phenoxy Acetic Acids, Benzoic Acids, and Pyridines) and Amino Acid Synthesis Inhibitors (Imidazolinones, Sulfonylureas, Sulfonamides, and glyphosate.)

Herbicidal cutting line should not be used in applications where the vegetation is desirable, such as lawns. Inadvertent use of the herbicidal cutting line will damage treated sections of lawn. To prevent inappropriate use, herbicidal cutting line is color-coded to distinguish conventional cutting line from herbicidal cutting line.

Herbicidal cutting line is not suitable for trimming desired plants and in this application should be replaced with conventional cutting line. To facilitate cutting line exchange, herbicidal cutting line is stored on a separate spool. To change cutting line, spools are exchanged.

Herbicidal cutting line provides an effective means for permanent removal of unwanted vegetation. Herbicidal cutting line can be used with the same ease as conventional cutting line but the simultaneous herbicide application reduces vegetation regrowth. Trimmed areas remain vegetation-free for extended periods due to herbicide activity.

Herbicidal cutting line provides a practical alternative to herbicide spraying. Cut vegetation remnants can be swept away. The simultaneous herbicide application reduces vegetation regrowth. The present invention eliminates spills, overfills, and drips associated with herbicide spraying and can be used with existing line trimmers.

Operation

The herbicidal cutting line is used with line trimmers in the same manner as conventional cutting line, however, care must be taken to trim only plants that are to be removed permanently. As vegetation is cut, herbicide residue remains on the rooted plant remnant, preventing regrowth.

Typical applications include clearing vegetation in drive ways, in sidewalks, against buildings, between pavers, and against retainer walls. The simultaneous herbicide application prevents weed regrowth. The cutting action allows for immediate removal by sweeping with a brush.

In some situations, herbicidal cutting line can be used to remove weeds growing among desirable vegetation. Weeds often grow higher than desirable vegetation such as ivy, lawn grass, and flowers. The trimmer can be used to cut unwanted vegetation at a height above the desirable vegetation. Since herbicide is applied only to cut vegetation, tall growing weeds are herbicide treated while shorter desirable plants remain untreated.

In each of the foregoing applications, herbicidal cutting line requires less herbicide than spraying since herbicide goes directly to the plant. Moreover, since the present invention eliminates herbicide drips and spills, inadvertent effects on the environment are minimized.

Conclusions, Ramifications, and Scope

Accordingly, the reader will see that herbicidal cutting line provides an easy means of vegetation removal. The preferred embodiment comprises a cutting-line core 13, a herbicidal coating 15 and a protective shield 17.

The ease of use and simplicity of the herbicidal cutting line make it attractive for small-scale residential applications. The cutting line can be used with existing line trimmers.

Herbicidal cutting line provides a sensible approach for vegetation removal that is both environmentally sound and practical.

Although the description above contains many specificities, these should not be construed as limiting the scope of the invention but as merely providing illustrations of some of the presently preferred embodiments of this invention. For example, the cutting line may contain a herbicidal core rather than a herbicidal coating.

Thus the scope of the invention should be determined by the appended claims and their legal equivalents, rather than by the examples given.

What is claimed is:

1. A cutting line, comprising an elongate filament suitable for use in rotating line trimmers, said filament being coated or impregnated with herbicide which is releasable by the trimming action.

2. The cutting line of claim 1 wherein the filament is color-coded to identify the herbicide from a plurality of herbicides.

3. The cutting line of claim 1 wherein the filament includes an outer coating of a substantially impermeable material.

4. The cutting line of claim 1 wherein the filament is a polymeric filament.

5. A system for applying a chemical to vegetation, comprising: a supply of a filament, which includes a biologically-active chemical; and a trimmer mechanism coupled to the supply of filament, the trimmer mechanism rotating a working end of the filament at a rate sufficient to trim vegetation on contact therewith, wherein such trimming action applies the chemical to the trimmed vegetation.

6. The system of claim 5 wherein the chemical is a herbicide.

7. The system of claim 5 wherein the filament is color-coded to identify the chemical from a plurality of chemicals.

8. The system of claim 5 wherein the chemical is impregnated into the filament.

9. The system of claim 5 wherein the chemical is coated onto the filament.

10. The system of claim 5 wherein the filament is a polymeric filament.

11. The system of claim 5 wherein the filament includes an outer coating of a substantially impermeable material.

12. A system for applying a herbicide to vegetation, comprising: a supply of a polymeric filament, which includes an integrated herbicide; and a trimmer mechanism coupled to the filament, the trimmer mechanism rotating a working end of the filament at a rate sufficient to trim vegetation on contact therewith, wherein such trimming action applies the herbicide to the trimmed vegetation.

13. The system of claim 12 wherein the filament is color-coded to identify the herbicide from a plurality of herbicides.

14. The system of claim 12 wherein the herbicide is impregnated within the filament.

15. The system of claim 12 wherein the filament includes an outer coating of a substantially impermeable material.

16. The method of claim 12 wherein the filament is a polymeric filament.

17. A method for applying a chemical to vegetation, comprising:

Supplying a filament, which includes a biologically-active chemical; coupling a trimmer mechanism to the supplied filament, and operating the trimmer mechanism to rotate a working end of the filament at a rate sufficient to trim vegetation on contact therewith, wherein such trimming action applies the chemical to the trimmed vegetation.

18. The method of claim 17 wherein the chemical is a herbicide.

19. The method of claim 17 wherein the filament is color-coded to identify the chemical from a plurality of chemicals.

20. The method of claim 17 wherein the chemical is impregnated into the filament.

21. The method of claim 17 wherein the chemical is coated onto the filament.

22. The method of claim 17 wherein the filament is a polymeric filament.

23. The method of claim 17 wherein the filament includes an outer coating of a substantially impermeable material.

24. A method for applying a herbicide to vegetation, comprising:

supplying a polymeric filament, which includes an integrated herbicide; coupling a trimmer mechanism to the filament; and operating the trimmer mechanism to rotate a working end of the filament at a rate sufficient to trim vegetation on contact threrwith, wherein such trimming action applies the herbicide to the trimmed vegetation.

25. The method of claim 24 wherein the filament is color-coded to identify the herbicide from a plurality of herbicides.

26. The method of claim 24 wherein the herbicide is impregnated within the filament.

27. The method of claim 24 wherein the herbicide is coated onto the the filament.

28. The method of claim 24 wherein the filament includes an outer coating of a substantially impermeable material.

* * * * *